US012564311B2

(12) United States Patent
Sharma

(10) Patent No.: US 12,564,311 B2
(45) Date of Patent: Mar. 3, 2026

(54) MEDICAL DEVICE ADAPTORS AND ASSOCIATED METHODS

(71) Applicant: Boston Scientific Medical Device Limited, Galway (IE)

(72) Inventor: Deepak Kumar Sharma, Muzaffarnagar (IN)

(73) Assignee: Boston Scientific Medical Device Limited, Galway (IE)

( * ) Notice: Subject to any disclaimer, the term of this patent is extended or adjusted under 35 U.S.C. 154(b) by 319 days.

(21) Appl. No.: 18/351,749

(22) Filed: Jul. 13, 2023

(65) Prior Publication Data

US 2024/0016368 A1     Jan. 18, 2024

Related U.S. Application Data

(60) Provisional application No. 63/368,693, filed on Jul. 18, 2022.

(51) Int. Cl.
A61B 1/00          (2006.01)
*A61M 39/10*          (2006.01)

(52) U.S. Cl.
CPC . A61B 1/00128 (2013.01); *A61M 2039/1077* (2013.01)

(58) Field of Classification Search
CPC ............ A61B 1/00128; A61B 1/00101; A61B 1/00089; A61B 1/00133; A61B 1/00137
See application file for complete search history.

(56) References Cited

U.S. PATENT DOCUMENTS

| | | | |
|---|---|---|---|
| 8,092,374 B2 | 1/2012 | Smith et al. | |
| 2011/0257477 A1 | 10/2011 | McWeeney | |
| 2013/0046138 A1 | 2/2013 | McLawhorn | |
| 2017/0049523 A1 | 2/2017 | Yoshii | |
| 2017/0112361 A1 | 4/2017 | Surti et al. | |
| 2021/0177244 A1* | 6/2021 | Weitzner ........... A61B 1/00066 | |
| 2021/0353274 A1 | 11/2021 | Reid et al. | |

* cited by examiner

*Primary Examiner* — Timothy J Neal
(74) *Attorney, Agent, or Firm* — Bookoff McAndrews PLLC

(57)          ABSTRACT

A medical device adaptor may comprise a distal portion, including a cap configured to be removably affixed to a distal end of a medical device and a channel extending through a lumen of the cap. The channel may be in fluid communication with a working channel of the medical device upon removably affixing the cap to the distal end of the medical device. The adaptor may further comprise a proximal portion including an actuator having a lumen. The actuator may be removably affixed to a proximal end of the medical device, such that the lumen of the proximal portion is configured to be in fluid communication with the working channel of the medical device. The medical device adaptor also may include one or more wires extending between the proximal portion and the distal portion. The one or more wires may be configured to articulate the channel of the distal portion.

19 Claims, 6 Drawing Sheets

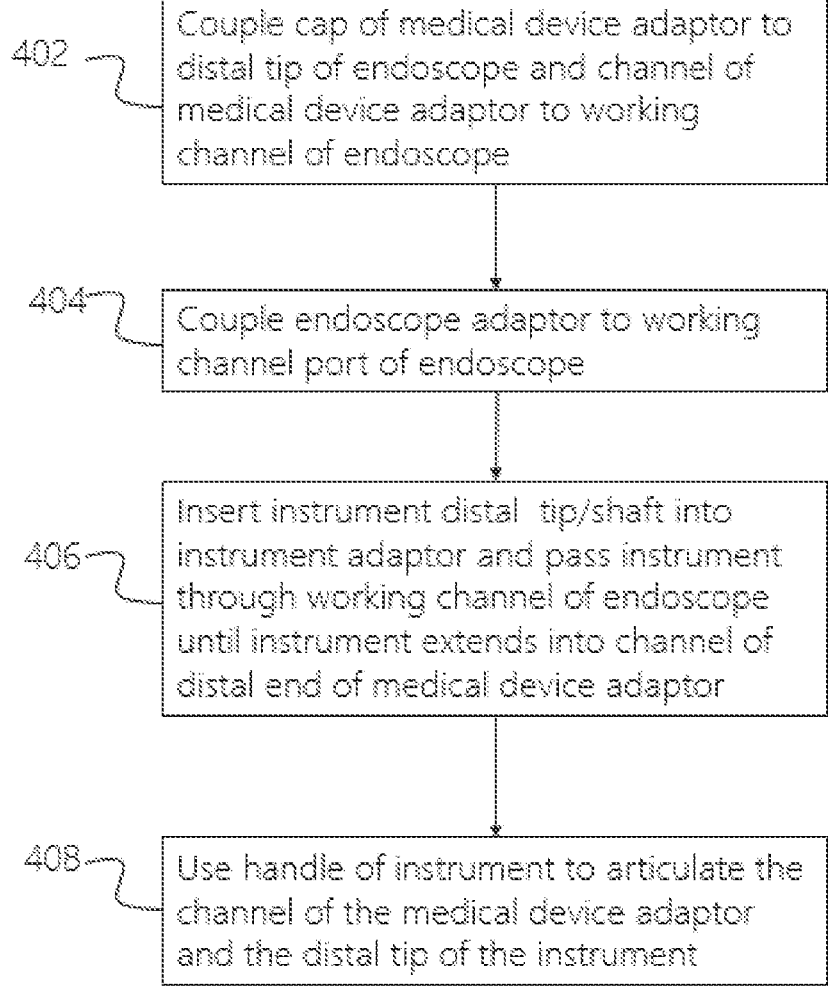

402 — Couple cap of medical device adaptor to distal tip of endoscope and channel of medical device adaptor to working channel of endoscope 404 — Couple endoscope adaptor to working channel port of endoscope 406 — Insert instrument distal tip/shaft into instrument adaptor and pass instrument through working channel of endoscope until instrument extends into channel of distal end of medical device adaptor 408 — Use handle of instrument to articulate the channel of the medical device adaptor and the distal tip of the instrument

FIG. 4

MEDICAL DEVICE ADAPTORS AND ASSOCIATED METHODS

CROSS-REFERENCE TO RELATED APPLICATIONS

This application claims the benefit of priority under 35 U.S.C. § 119 from U.S. Provisional Application No. 63/368,693, filed Jul. 18, 2022, which is incorporated by reference herein in its entirety.

TECHNICAL FIELD

The disclosure relates generally to devices, systems, and methods for medical device adaptors and associated methods. More specifically, aspects of the disclosure pertain to devices, systems, and/or methods for adaptors that enable articulation of instruments passed through medical devices, such as endoscopes.

BACKGROUND

During a medical procedure, an operator may navigate a medical device (e.g., an endoscope or other type of scope) to a site where a procedure (e.g., a treatment or a diagnostic procedure) is to be performed. To perform the procedure, the operator may extend one or more instruments through a working channel of an endoscope. A distal end of the instrument may extend from a distal opening of the working channel, at a distal end of a shaft of the endoscope. A proximal end of the instrument may extend proximally through a port of a handle of the endoscope. The operator may manipulate the instrument (e.g., using the proximal end of the instrument) in order to perform a procedure using the distal end of the instrument.

Although the endoscope through which the instrument(s) is/are passed may have articulation functionality, the instrument(s) may lack functionality to independently articulate, relative to the endoscope. A lack of articulation of the instrument(s) may render a procedure more difficult, more time-consuming, more costly, and/or less effective/accurate than a procedure would be were the instrument(s) capable of independent articulation. Therefore, a need exists for devices, systems, and/or methods for adaptors that enable articulation of instruments passed through medical devices, such as endoscopes.

SUMMARY

A medical device adaptor may comprise: a distal portion including: a cap configured to be removably affixed to a distal end of a medical device; and a channel extending through a lumen of the cap. The channel may be configured to be in fluid communication with a working channel of the medical device upon removably affixing the cap to the distal end of the medical device. The medical device adaptor may further comprise a proximal portion including an actuator having a lumen. The actuator may be configured to be removably affixed to a proximal end of the medical device, such that the lumen of the proximal portion is configured to be in fluid communication with the working channel of the medical device. The medical device adaptor may include one or more wires extending between the proximal portion and the distal portion. The one or more wires are configured to articulate the channel of the distal portion relative to the distal end of the medical device.

Any of the examples described herein may have any of the following features in any combination. The actuator may include a ball. One or more wires may be attached to the ball. A tube may extend proximally from the ball. The tube may be configured to receive a shaft of a medical instrument. The actuator may be configured to be actuated by movement of a handle of the medical instrument. The proximal portion may include a connector distal of the ball. One or more wires may pass through an internal lumen of a first portion of the connector and extend outside of an outer surface of a second portion of the connector. The proximal portion may include a housing. The housing may include one or more protrusions. The ball may be disposed within the housing contacting the one or more protrusions. At least a portion of the one or more wires may include a coil pipe thereabout. The one or more wires may be configured to extend along an outer surface of a shaft of the medical device. The one or more wires may include at least three wires. Each of the one or more wires may extend through a respective lumen formed in a wall of the cap. Each lumen in the wall of the cap may extend from a proximal surface of the cap to a distal surface of the cap. The channel may be flexible. The proximal portion may be configured to removably attach to a port of the working channel of the medical device.

In an additional or alternative example, a medical device adaptor may comprise a cap configured to be removably affixed to a distal end of a medical device. The cap may include a plurality of wire lumens. The medical device adaptor may further include a channel configured to be in fluid communication with a working channel of a medical device upon removably affixing the cap to the distal end of the medical device and a plurality of wires, each of the plurality of wires extending through a respective lumen of the plurality of wire lumens extending from a proximal surface of the cap to a distal surface of the cap. Each of the plurality of wires may be coupled to the channel. The cap may include an annular wall defining a central lumen. The channel may extend through the central lumen.

Any of the examples described herein may have any of the following features in any combination. The plurality of wire lumens may extend through the annular wall, approximately parallel to a central longitudinal axis of the central lumen.

In an additional or alternative example, a medical method may comprise attaching a distal cap of a medical device adaptor to a distal tip of a medical device, such that a channel of the distal cap is in fluid communication with a working channel of the medical device; attaching an actuator of the medical device adaptor to a port of the working channel of the medical device; inserting a shaft of an instrument into a lumen of the actuator, into the working channel of the medical device and into the channel of the distal cap; and moving a handle of the instrument in order to articulate the channel of the distal cap and the shaft of the instrument.

Any of the examples described herein may include any of the following features. Moving the handle may apply tension to at least one wire extending between the actuator and the channel of the distal cap.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate examples of this disclosure and together with the description, serve to explain the principles of the disclosure.

FIG. 4 shows a flow chart of an exemplary medical method.

DETAILED DESCRIPTION

The medical device adaptor disclosed herein may include a proximal ball joint interface and a distal cap. The ball joint interface may connect to a working channel port of an endoscope, and the distal cap may connect to a distal tip of the endoscope. Steering wires may extend between the ball joint interface and the distal tip. For example, the steering wires may extend over a shaft of the endoscope. An instrument may be inserted into a lumen of the ball joint interface, pass through the working channel of the endoscope, and extend through a lumen of the distal tip of the medical device adaptor. An operator may move a handle or shaft of the instrument extending proximally from the ball joint interface, for example, akin to moving a joystick. This movement of the instrument may, in turn, cause the steering wires to articulate the lumen of the distal tip of the medical device adaptor. Thus, the disclosed medical device adaptor may facilitate articulation of an instrument that otherwise lacks independent articulation.

Figure 1:
FIG. 1 depicts a perspective view of an exemplary medical device adaptor installed on an exemplary endoscope.

As shown in FIG. 1, a medical device such as an endoscope 10 may include a handle 12 and a shaft 14. Although endoscopes are referenced herein, it will be appreciated that the disclosure encompasses any medical devices having a working channel extending from a proximal end to a distal end, such as ureteroscopes, duodenoscopes, gastroscopes, endoscopic ultrasonography ("EUS") scopes, colonoscopes, bronchoscopes, laparoscopes, arthroscopes, cystoscopes, aspiration scopes, sheaths, or catheters. Handle 12 may include a plurality of actuators 16 for controlling aspects of endoscope 10. Actuators 16 may include actuators for steering/articulating (e.g., knobs, levers, sliders, buttons, joysticks, etc.) shaft 14, actuators for delivering fluids and/or suction (e.g., valves), locks, elevator control actuators, image capture buttons, or any other actuator. Some or all of actuators 16 may control functions of a distal tip 18 of endoscope 10. Wires, cables, and/or tubing may extend from handle 12 to distal tip 18 for providing such control of distal tip 18 via actuators 16. A working channel (not shown) may extend from a working channel port 20 of handle 12, through shaft 14, to an opening of distal tip 18. Instruments (such as an instrument 50, described below), guidewires, or other devices may be passed through port 20, through the working channel, and out of the opening of distal tip 18. An umbilicus 22 may connect handle 12 to external equipment, such as controllers, one or more displays, and/or sources of fluids or suction.

Figures 2A, 2B:
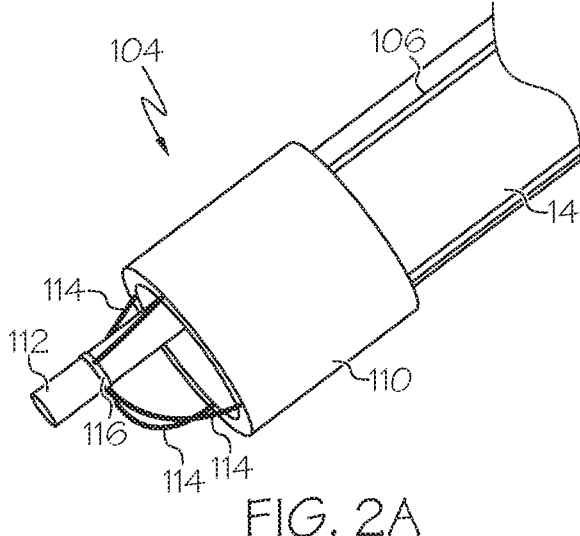
FIGS. 2A and 2B depict perspective views of a distal end of the exemplary medical device adaptor of FIG. 1.
Figure 2C:
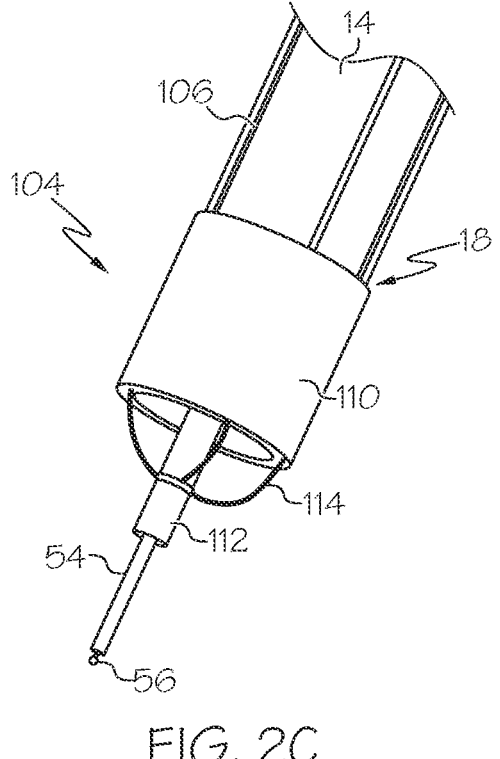
FIGS. 2C and 2D depict perspective views of the distal end of the exemplary medical device adaptor of FIGS. 2A and 2B installed on a distal end of an exemplary endoscope, with the distal end of the exemplary medical device adaptor of FIGS. 2A and 2B in an unarticulated configuration (FIG. 2C) and an articulated configuration (FIG. 2D).

As shown in FIG. 1, an instrument 50 may be used in conjunction with endoscope 10. As depicted in FIG. 1, instrument 50 may include an electrosurgical knife having a distal tip 56, as shown in FIG. 2C. However, a type of instrument 50 depicted in FIG. 1 is merely exemplary and any type of instrument, tool, or other device may be utilized (e.g., grasper, stapler, ablation device, snare, tome, suturing device, needle, or knife). For example, where instrument 50 is a tome or other instrument used during endoscopic retrograde cholangiopancreatography ("ERCP"), a medical device adaptor 100 may be used to facilitate ERCP, including cannulating a papilla of a subject. Instrument 50 may include a handle 52 and a shaft 54. Shaft 54 may terminate in a distal tip 56 (see FIG. 2C). Shaft 54 of instrument 50 may extend through the working channel of endoscope 10, via port 20.

As described herein, medical device adaptor 100 may interface with endoscope 10 and instrument 50 to provide articulation of distal tip 56 of instrument 50. Absent medical device adaptor 100, instrument 50 may otherwise lack an ability to articulate independently of endoscope 10. As used herein, the term "articulation" refers to moving a distal portion of a device/instrument (e.g., a shaft of the device/instrument), such that the distal portion is transverse to a more proximal portion of said device/instrument. For example, articulation may include bending the distal portion of the shaft, such that the distal portion of the shaft is transverse to a more proximal portion of the shaft. The shaft may adopt, for example, a curved shape when articulated. "Passive articulation" may include articulation that results from forces a body lumen exerts on the device/instrument. "Active articulation" may refer to articulation controlled by an operator using actuator(s) or the like. Unless otherwise stated, "articulation" as used herein refers to active articulation.

Figure 2D:
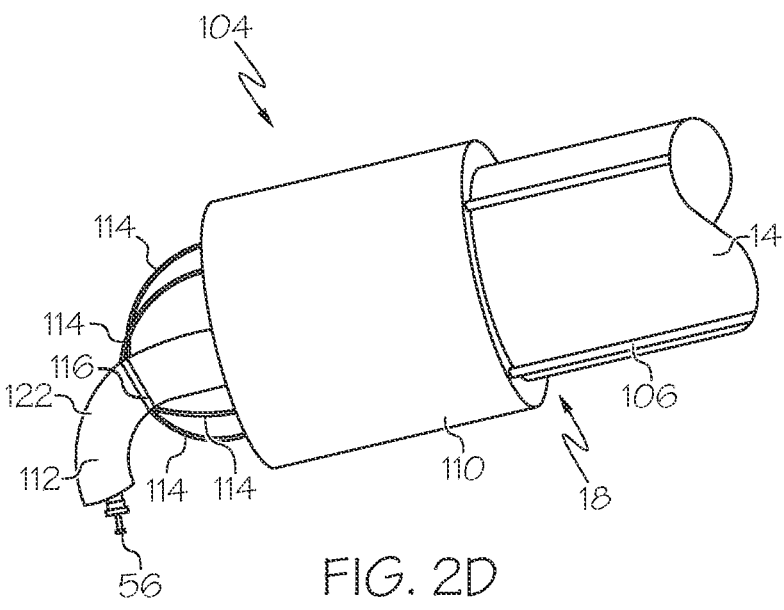

As shown in FIG. 1, medical device adaptor 100 may include a proximal portion 102 and a distal portion 104. A plurality of wires or cables 106 may extend between proximal portion 102 and distal portion 104. FIGS. 2A-2D depict aspects of distal portion 104, and FIGS. 3A-3E depict portions of proximal portion 102. As shown in FIGS. 1 and 2A-2D, distal portion 104 may include a cap 110. Cap 110 may be configured to fit over at least a portion of distal tip 18 of endoscope 10, as shown in FIGS. 2C and 2D to removably affix cap 110 to distal tip 18. Alternatively, cap 110 may be permanently fixedly attached to distal tip 18. For example, cap 110 may include an annular wall that defines a lumen 111. Distal tip 18 may be inserted into lumen 111 (FIG. 2B). An inner surface of cap 110 may mate with distal tip 18 via, e.g., a friction fit. Alternatively, mating features may be disposed on cap 110 and/or distal tip 18 to facilitate securing cap 110 to distal tip 18. Distal tip 18 may be inserted only part-way into cap 110, such that a distal end of cap 110 extends distally of distal tip 18.

A channel 112 (e.g., a tube) may extend through lumen 111 of cap 110. Channel 112 may attach to the working channel of endoscope 10, such that a lumen defined by the working channel of endoscope 10 is in fluid communication with a lumen defined by channel 112. Cap 110 and channel 112 may be configured such that, in configurations in which cap 110 is attached to distal tip 18, channel 112 may be aligned with a distal opening of the working channel. Portions of channel 112 may be rigid. For example, channel 112 may include a tube (e.g., a metal tube). In examples, only a proximal portion of channel 112 may include such a metal tube, which may impart rigidity to the proximal portion of channel 112. A stiffness of the metal tube may be such that channel 112 remains in alignment with the working channel of the endoscope. Additionally or alternatively, channel 112 may be partially inserted into a distal opening of the working channel when distal tip 18 is inserted into cap 110. In examples, a proximal end 124 of channel 112 may have a friction fit within the working channel. A shape of channel 112 may be configured to mate with the distal opening of the working channel. For example, as shown in FIGS. 2A-2D, channel 112 may be round (i.e., with a circular cross-section) so as to mate with a round distal opening of the working channel. Alternatively, channel 112 and the distal opening of the working channel may have different shapes. When fixed to the working channel of endoscope 10, channel 112 may be axially fixed relative to cap 110.

As shown in FIGS. 2A-2D, channel 112 may be off-centered within cap 110, such that a central longitudinal axis of channel 112 in the unarticulated configuration of FIG. 2A is approximately parallel to but not coaxial with a central longitudinal axis of cap 110. Such an off-centered arrangement of channel 112 and cap 110 may correspond to a position of the distal opening of the working channel of endoscope 10. Alternative arrangements may exist for alternative endoscopes 10. For example, distal portion 104 may include a custom configuration for a particular endoscope 10. Alternatively, a single distal portion 104 may be usable with multiple types of endoscopes 10 (or other devices). A distal end 122 of channel 112 may extend distally of a distal end of cap 110. As shown in FIG. 2A, distal end of cap 110 may be open, such that cap 110 is approximately tubular. Alternatively, a distal end of cap 110 may be partially closed, for example, including a distal cover, with an opening formed therein through which channel 112 passes.

As shown in FIG. 2B, cables 106 may extend through lumens 118 formed in the wall of cap 110. The lumens 118 may extend longitudinally through the annular wall of cap 110, from a proximal surface of cap 110 to a distal surface of cap 110. For example, longitudinal axes of the lumens 118 may be substantially parallel to a longitudinal axis of lumen 111. Although the term "cable" is used herein, it will be appreciated that wires, filaments, or alternative structures may be utilized in place of cables. In one example, as shown in FIGS. 2A-2D, cables 106 may include Bowden cables (i.e., a cable or wire 114 with a coil pipe or similar structure thereabout). The coil pipes may abut a proximal end of cap 110 and may be fixed to the proximal end of cap 110. Alternatively, coil pipes of cables 106 may be fixed within the lumens 118 formed in the wall of cap 110. As shown in FIG. 2B, medical device adaptor 100 may include four cables 106, each including a coil pipe and a wire 114 extending therethrough. However, alternative numbers of cables (e.g., one cable, two cables, or three cables) may be utilized. Wires 114 may extend distally past a coil pipe of cables 106. For example, only wires 114 may extend through lumens 118. Wires 114 may be able to move relative to the coil pipes. For example, wires 114 may be movable proximally and distally through the coil pipes. Wires 114 also may be movable proximally and distally relative to the lumens 118 extending through the wall of cap 110. Distal portions of wires 114 may extend distally of a distal end of cap 110. In alternatives, wires or cables that are not Bowden cables may be utilized. In such examples, an entirety of the wires or cables may extend through the lumens 118 extending through the wall of cap 110 and may be movable relative to cap 110.

A distal end of each wire 114 may be coupled/fixed to channel 112. For example, the distal end of each wire 114 may be fixed to a portion of channel 112 that extends distally of cap 110. Each wire 114 may be coupled (e.g., fixed) to a ring 116 that extends about channel 112. Ring 116 may be fixed to channel 112, for example, around an external circumference of channel 112. Alternatively, wires 114 may be fixed directly to channel 112. Channel 112 may include a flexible material, such that force(s) exerted by one or more of wires 114 may cause channel 112 to bend/articulate (as show in FIG. 2D). In alternatives, channel 112 may include one or more articulation joints that facilitate bending of channel 112.

Shaft 54 of instrument 50 may extend through the working channel of endoscope 10 and through a lumen defined by channel 112. As shown in FIG. 2C, distal tip 56 of instrument 50 may extend distally of a distal end of channel 112. In the unarticulated configuration of medical device adaptor 100 shown in FIG. 2C, channel 112 may be approximately straight and may extend approximately parallel to a central longitudinal axis of cap 110.

As shown in FIG. 2D, when one or more of wires 114 are moved proximally (via the mechanisms discussed above and below), the wire(s) 114 may pull on channel 112, causing it to articulate/bend. The bending of channel 112 may, in turn, bend shaft 54 of instrument 50 (which may be flexible). Thus, channel 112 may change an orientation/position of distal tip 56 of instrument 50. In the configuration of FIG. 2D, distal end 122 of channel 112 may have a central longitudinal axis that is transverse to a central longitudinal axis of proximal end 124 of channel 112.

Figure 3A:
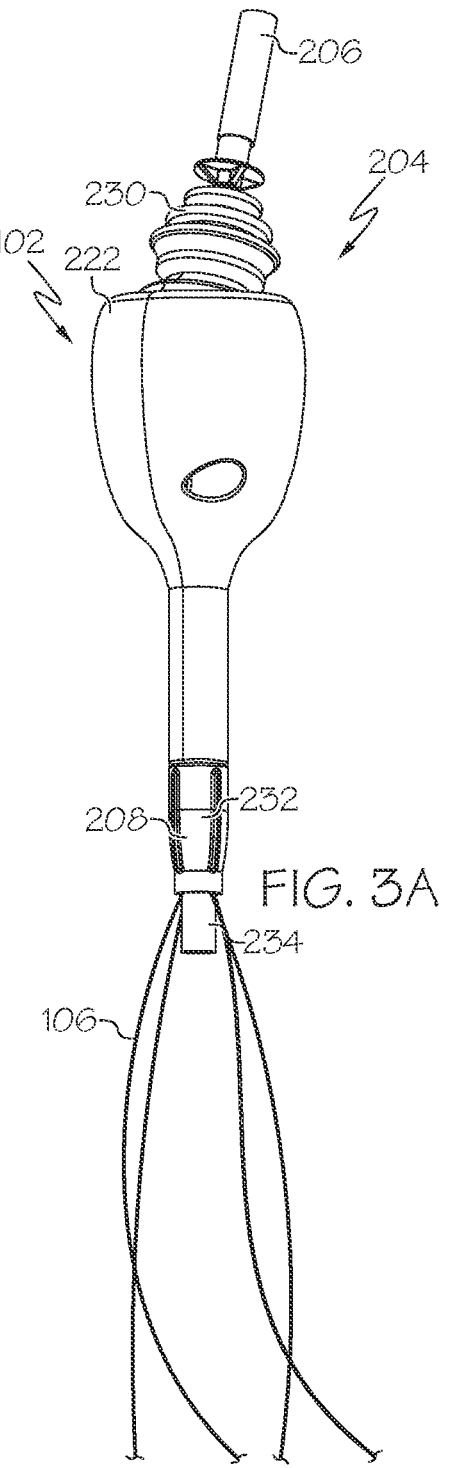
FIG. 3A shows a proximal portion of the medical device adaptor of FIG. 1.
Figure 3B:
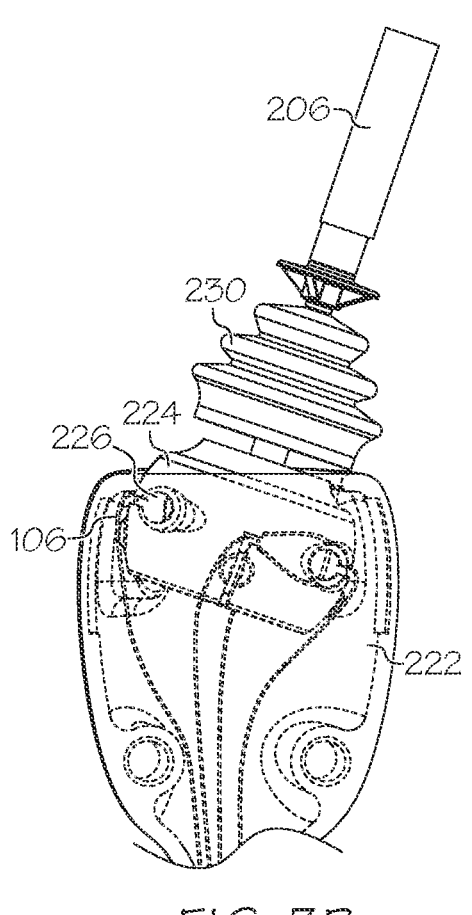
FIG. 3B shows a portion of a joint of the proximal portion of the medical device adaptor of FIG. 3A.
Figures 3C, 3D, 3E:
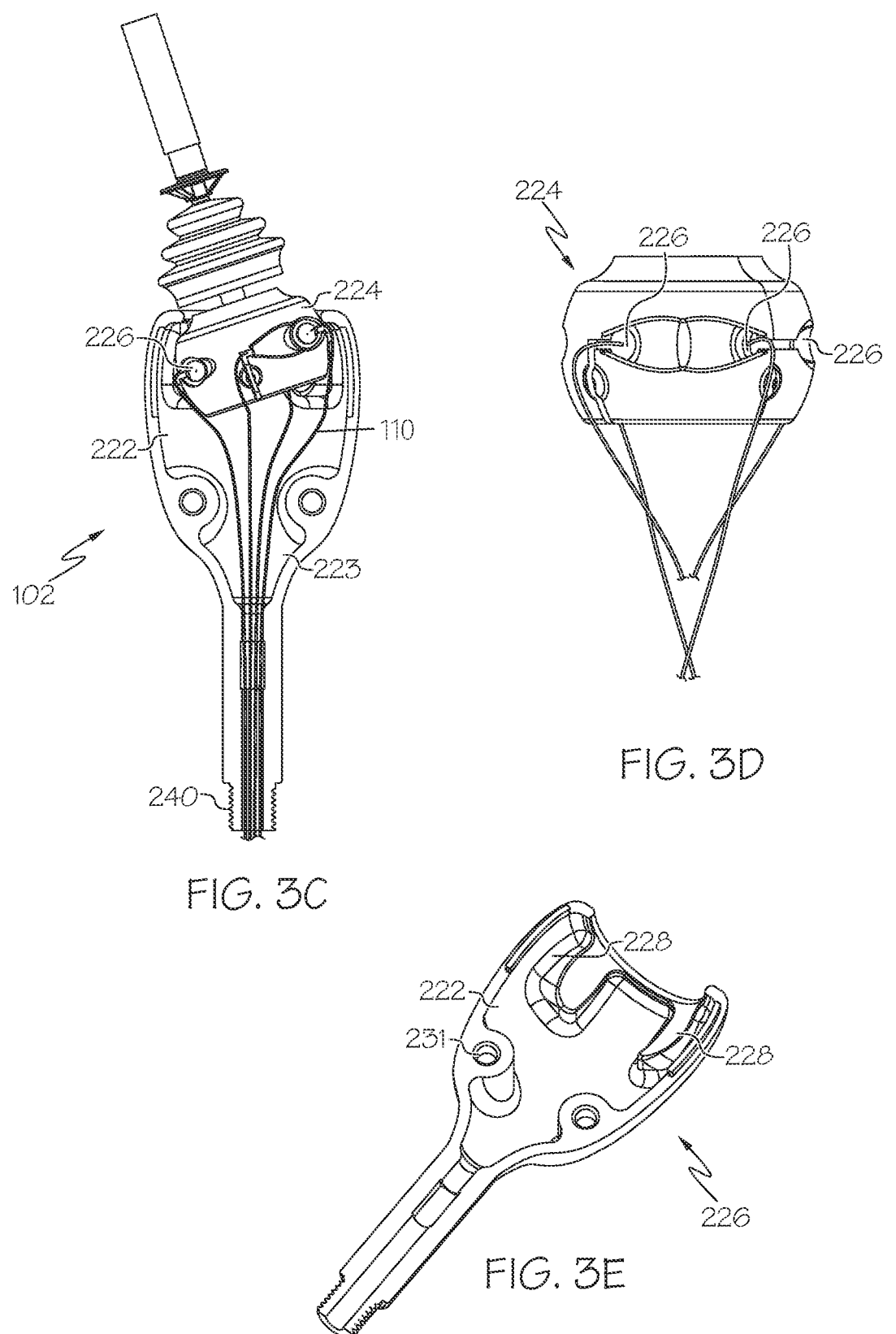
FIG. 3C shows the joint of FIG. 3B with a portion of a housing removed.
FIG. 3D shows an exemplary ball and exemplary wires of the joint of FIG. 3A.
FIG. 3E shows a portion of a housing of the joint of FIG. 3A.

FIGS. 3A-3E depict aspects of proximal portion 102 of medical device adaptor 100. Proximal portion 102 may include a ball joint interface, as discussed below. Proximal portion 102 may include an actuator, such as a ball and socket joint 204. Proximal portion 102 also may include an instrument adaptor 206 for receiving instrument 50, an endoscope adaptor 210 (FIG. 1) for connecting proximal portion 102 to the working channel port 20 of endoscope 10, and a connector 208 for connecting endoscope adaptor 210 (FIG. 1) to ball and socket joint 204. FIGS. 3A-3C show ball and socket joint 204 in an articulated configuration (a configuration that causes channel 112 to articulate as, for example, in FIG. 2D). FIG. 3A shows ball and socket joint 204 with all elements solid. FIG. 3B shows a portion of ball and socket joint 204 with elements within a housing 222 shown in broken lines. FIG. 3C shows a portion of ball and socket joint 204 with a half of housing 222 omitted to show details internal to housing 222.

As shown in FIGS. 3A-3C, ball and socket joint 204 may include housing 222 and a ball 224. As described below, housing 222 may function as a "socket." FIG. 3D shows further details of ball 224. FIG. 3E shows one half of housing 222. Proximal ends of cables 106 may be fixed to ball 224. For example, wires (e.g., wires 114) of cables 106 may be fixed to ball 224. Ball 224 may include a plurality of openings 226 for receiving the proximal ends of cables 106. The proximal ends of cables 106 may include crimps or other structures for being received in openings 226. Additionally or alternatively, adhesives, plugs, mating structures, pins, rivets, or other fasteners/elements may be utilized to attach the proximal ends of cables 106 to openings 226. Cables 106 may be attached equidistant from one another about ball 224. For example, four cables 106 may be attached at approximately 90 degree intervals about ball 224 (e.g., corresponding to up, down, left, and/or right directions). For medical device adaptors 100 having three cables 106, cables 106 may be positioned at 120 degree intervals from one another. For medical device adaptors 100 having two cables 106, cables 106 may be positioned 180 degrees opposing one another. Ball 224 may have an approximately round shape. For example, ball 224 may have a shape similar to an oblate spheroid. The shape of ball 224 is merely exemplary, and any suitable shape may be utilized.

Housing 222 may receive ball 224. Housing 222 may include a plurality of protrusions 228, on which ball 224 may rest (FIG. 3E). Protrusions 228 may taper radially inward, toward a central longitudinal axis of housing 222, along a distal direction toward working channel port 20. Protrusions 228 may have curved surfaces that may generally correspond to a shape of ball 224. Ball 224 may be movable relative to protrusions 228, but protrusions 228 may contact ball 224 and inhibit ball 224 from moving axially toward working channel port 20. Additionally, housing 222 may taper from a proximal end toward a distal end of housing 222. The taper of housing 222 may facilitate receiving ball 224 at the proximal end of housing 222 and connecting to connector 208 at the distal end of housing 222. The taper also may retain ball 224 within a proximal portion of housing 222. Housing 222 may include two halves (FIG. 3E depicting one such half). The halves may be joined using holes 231. For example, a fastener or adhesive may extend through holes 231 to retain the halves of housing 222 together.

As seen in FIGS. 3A-3C, ball 224 may be fixed to instrument adaptor 206 via a ridged element 230. Ridged element 230 may be shaped akin to, for example, a bellows. Ridged element 230 may be flexible or rigid. Ridged element 230 may serve as a visual indicator to an operator that adaptor 206 functions akin to a joystick. Operators may be familiar with structures typically associated with joysticks and so may appreciate how medical device adaptor 100 operates by noting the visual indicator.

Instrument adaptor 206 may define a lumen, such that distal tip 56 and shaft 54 of instrument 50 may be inserted into instrument adaptor 206. For example, instrument adaptor 206 may include a tube (e.g., a rigid tube). The lumen may extend through ridged element 230 and ball 224 (or an interior of ball 224 may otherwise be open) such that the lumen of instrument adaptor 206 is in fluid communication with an interior of housing 222. A distal portion of housing 222 (a portion closer to working channel port 20) may define a housing lumen 223 for receiving distal tip 56/shaft 54 of instrument 50 and cables 106 (or wires 114 of cables 106) therethrough (FIG. 3C).

Connector 208 may attach to a distal end of housing 222. For example, connector 208 may screw onto threads 240 of the distal end of housing 222. Connector 208 may have a proximal portion 232 and a distal portion 234. Cables 106

(or wires 114 of cables 106) and distal tip 56/shaft 54 of instrument 50 may extend through a proximal opening of proximal portion 232 of connector 208 and into a lumen of proximal portion 232. Distal tip 56/shaft 54 may extend through a lumen of distal portion 234, into a lumen of endoscope adaptor 210, and into working channel port 20 of endoscope 10. Cables 106 (or wires 114 of cables 106) may extend through opening(s) between proximal portion 232 and distal portion 234 of connector 208, such that cables 106 (or wires 114 of cables 106) extend inside of proximal portion 232 and externally of an outer surface of distal portion 234, as shown in FIG. 3A. In some examples, coil pipes of cables 106 may have proximal ends at or near a distal portion of proximal portion 232. Cables 106 may remain external to endoscope 10 and extend along an outer surface of shaft 14 to distal portion 104 of medical device adaptor 100. In alternatives, cables 106 may be received within a sheath (not shown) configured to fit over shaft 14.

A method of using medical device adaptor 100 is described below and illustrated in FIG. 4. In step 402, to attach medical device adaptor 100 to endoscope 10, cap 110 of distal portion 104 may be attached to distal tip 18, such that proximal end 124 of channel 112 is aligned with an opening of the working channel of endoscope 10. In step 404, endoscope adaptor 210 of proximal portion 102 may then be attached to working channel port 20 of endoscope 10 (FIG. 1). Alternatively, steps 402 and 404 may be performed in a reverse order. After medical device adaptor 100 is thus attached to endoscope 10, the lumen of instrument adaptor 206 may be in fluid communication with the lumen of the working channel of endoscope 10, via the lumen of ball 224, the lumen(s) of connector 208, the lumen of endoscope adaptor 210, and port 20. The lumen of the working channel of endoscope 10 may, in turn, be in fluid communication with channel 112.

Thereafter, in step 406, instrument 50 may be inserted into instrument adaptor 206, passed through proximal portion 102 of medical device adaptor 100 (through instrument adaptor 206, ball 224, housing 222, connector 208, and endoscope adaptor 210), passed through working channel port 20 of endoscope 10, through the working channel of endoscope 10, and into channel 112 of distal portion 104. Distal tip 56 of instrument 50 may extend distally of a distal opening of channel 112.

Thereafter, in step 408, an operator may manipulate handle 52 of instrument 50 in order to articulate channel 112 and, thus, distal tip 56. For example, the operator may move handle 52 up, down, left, or right to articulate channel 112 upward, downward, leftward, or rightward, respectively. Features of ball 224, housing 222, or other elements of proximal portion 102 may restrict movement of instrument adaptor 206 and/or ball 224 to pre-defined directions (e.g., up, down, left, right). In alternatives, ball 224 and/or instrument adaptor 206 may be movable in any direction (e.g., 360 degree range of motion). As the operator moves the handle 52, shaft 54 of instrument 50 may exert a force on instrument adaptor 206 and, in turn, ball 224 (which is fixedly connected to instrument adaptor 206). Movement of ball 224 may cause movement of cables 106. For example, movement of ball 224 may apply tension to one or more cables 106. Cables 106 may exert corresponding forces on channel 112 via wires 114 (e.g., via ring 116). Articulation of channel 112 may, in turn, exert forces on shaft 54 of instrument 50, thereby articulating distal tip 56 of instrument 50.

An operator also may move handle 52 axially (in a proximal or distal direction) to move distal tip 56 proximally or distally. The operator also may rotate handle 52 about a longitudinal axis of handle 52 in order to rotate distal tip 56. Thus, medical device adaptor 100 may provide for four degrees of freedom for non-articulating instruments. The articulation of instrument 50 may be independent of an articulation of shaft 14. An operator may perform the articulation with a single hand and may perform multiple types of movement (e.g., axial, rotational, articulating) of instrument 50 simultaneously. Medical device adaptor 100 may provide an intuitive interface that has a low learning curve and does not require extensive training. An operator's hand movements may mimic movement of distal tip 56 of instrument 50.

Medical device adaptor 100 may have a low cost and may be disposable (i.e., a single use device). Medical device adaptor 100 also may provide for a quick setup and may be used with multiple types of endoscopes and/or multiple types of instruments. The manual platform of medical device adaptor 100 does not require costly robotics. Medical device adaptor 100 may be adaptable for a bimanual platform. In such aspects, medical device adaptor 100 may include two (or more) channels 112, configured to align with respective two (or more) working channels of endoscope 10. Each channel 112 may be associated with its own set of cables 106. For example, each channel 112 may be associated with four cables 106, as discussed above, so that four cables 106 are coupled to each of the channels 112, allowing for steering of each channel 112, as described above. Endoscope 10 may further include two (or more) handles 12, each including a working channel port 20 for a respective working channel. The configuration of endoscope 10 is not so limited, and it will be appreciated that other arrangements (e.g., a single handle 12 having a plurality of working channel ports 20) are contemplated within the scope of the disclosure.

In some aspects, medical device adaptor 100 may provide for omni-steerability, for example, in a circle or semicircle (movement of handle 52 of instrument 50 in a circle/ semicircle and corresponding movement of distal tip 56 of instrument 50). To provide for such omni-steerability, medical device adaptor 100 may include at least three cables 106. In examples, three cables 106 may be arranged such that cables 106 extend through lumens 118 of cap 110 at approximately 120 degree intervals (i.e., lumens 118 are evenly spaced about a circumference of cap 110), and wires 114 may attach to ring 116 at approximately the same interval. Medical device adaptor 100 may limit operator-dependent aspects of a medical procedure. For example, whereas, without medical device adaptor 100, an outcome/length/etc. of a procedure may depend heavily upon operator skill, medical device adaptor 100 may facilitate shorter, successful procedures across technicians through ease of use.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

I claim:

1. A medical device adaptor comprising:
a distal portion including:
a cap configured to be removably affixed to a distal end of a medical device; and
a channel extending through a lumen of the cap, wherein the channel is configured to be in fluid communication with a working channel of the medical device upon removably affixing the cap to the distal end of the medical device;
a proximal portion including an actuator having a lumen, wherein the actuator is configured to be removably affixed to a proximal end of the medical device, such that the lumen of the proximal portion is configured to be in fluid communication with the working channel of the medical device; and
one or more wires extending between the proximal portion and the distal portion, wherein the one or more wires are configured to articulate the channel of the distal portion relative to the distal end of the medical device.

2. The medical device adaptor of claim 1, wherein the actuator includes a ball.

3. The medical device adaptor of claim 2, wherein the one or more wires are attached to the ball.

4. The medical device adaptor of claim 2, wherein a tube extends proximally from the ball.

5. The medical device adaptor of claim 4, wherein the tube is configured to receive a shaft of a medical instrument.

6. The medical device adaptor of claim 5, wherein the actuator is configured to be actuated by movement of a handle of the medical instrument.

7. The medical device adaptor of claim 2, wherein the proximal portion includes a connector distal of the ball, wherein the one or more wires pass through an internal lumen of a first portion of the connector and extend outside of an outer surface of a second portion of the connector.

8. The medical device adaptor of claim 2, wherein the proximal portion includes a housing, wherein the housing includes one or more protrusions, and wherein the ball is disposed within the housing contacting the one or more protrusions.

9. The medical device adaptor of claim 1, wherein at least a portion of the one or more wires includes a coil pipe thereabout.

10. The medical device adaptor of claim 1, wherein the one or more wires are configured to extend along an outer surface of a shaft of the medical device.

11. The medical device adaptor of claim 1, wherein the one or more wires include at least three wires.

12. The medical device adaptor of claim 1, wherein each of the one or more wires extends through a respective lumen formed in a wall of the cap.

13. The medical device adaptor of claim 12, wherein each lumen in the wall of the cap extends from a proximal surface of the cap to a distal surface of the cap.

14. The medical device adaptor of claim 1, wherein the channel is flexible.

15. The medical device adaptor of claim 1, wherein the proximal portion is configured to removably attach to a port of the working channel of the medical device.

16. A medical device adaptor comprising:
a cap configured to be removably affixed to a distal end of a medical device, wherein the cap includes a plurality of wire lumens, wherein the cap includes an annular wall defining a central lumen;
a channel configured to be in fluid communication with a working channel of the medical device upon removably affixing the cap to the distal end of the medical device, wherein the channel extends through the central lumen of the cap; and
a plurality of wires, each of the plurality of wires extending through a respective lumen of the plurality of wire lumens extending from a proximal surface of the cap to a distal surface of the cap, wherein each of the plurality of wires is coupled to the channel.

17. The medical device adaptor of claim 16, wherein the plurality of wire lumens extend through the annular wall, approximately parallel to a central longitudinal axis of the central lumen.

18. A medical method, comprising:

attaching a distal cap of a medical device adaptor to a distal tip of a medical device, such that a channel of the distal cap is in fluid communication with a working channel of the medical device;

attaching an actuator of the medical device adaptor to a port of the working channel of the medical device;

inserting a shaft of an instrument into a lumen of the actuator, into the working channel of the medical device and into the channel of the distal cap; and moving a handle of the instrument to articulate the channel of the distal cap and the shaft of the instrument.

19. The medical method of claim 18, wherein moving the handle applies tension to at least one wire extending between the actuator and the channel of the distal cap.

* * * * *